United States Patent [19]

Keil et al.

[11] Patent Number: 4,624,696
[45] Date of Patent: Nov. 25, 1986

[54] CYCLOHEXENONE DERIVATIVES AND THEIR USE FOR CONTROLLING UNDESIRABLE PLANT GROWTH

[75] Inventors: Michael Keil, Freinsheim; Rainer Becker, Bad Durkheim; Dieter Jahn, Edingen-Neckarhausen; Dieter Kolassa, Ludwigshafen; Ulrich Schirmer, Heidelberg; Wolfgang Will, Mannheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 785,756

[22] Filed: Oct. 9, 1985

[30] Foreign Application Priority Data

Oct. 11, 1984 [DE] Fed. Rep. of Germany ....... 3437238

[51] Int. Cl.[4] ..................... A01N 43/08; A01N 43/10; C07D 307/54; C07D 333/22
[52] U.S. Cl. ............................................ 71/88; 71/90; 71/91; 71/94; 546/275; 546/276; 546/283; 546/284; 548/127; 548/136; 548/143; 548/247; 549/13; 549/23; 549/59; 549/60; 549/347; 549/396; 549/414; 549/448; 549/472; 549/473
[58] Field of Search ...................... 549/13, 23, 59, 60, 549/347, 396, 414, 448, 472, 473; 548/127, 136, 143, 247; 546/275, 277, 283, 284; 71/88, 90, 91, 92, 94

[56] References Cited

U.S. PATENT DOCUMENTS

| | | | |
|---|---|---|---|
| 3,950,420 | 4/1976 | Sawaki et al. | 564/256 X |
| 3,989,737 | 11/1976 | Sawaki et al. | 564/256 X |
| 4,422,864 | 12/1983 | Becker et al. | 71/88 |
| 4,432,786 | 2/1984 | Loh | 71/90 |
| 4,440,566 | 4/1984 | Luo | 564/256 X |
| 4,511,391 | 4/1985 | Serban et al. | 549/23 X |
| 4,545,806 | 10/1985 | Jahn et al. | 71/88 |

FOREIGN PATENT DOCUMENTS

| | | |
|---|---|---|
| 136647 | 4/1985 | European Pat. Off. . |
| 136702 | 4/1985 | European Pat. Off. . |
| 3123312 | 12/1982 | Fed. Rep. of Germany . |
| 3239071 | 4/1984 | Fed. Rep. of Germany . |
| 129042 | 10/1979 | Japan . |

OTHER PUBLICATIONS

Tetrahedron Letters No. 29, pp. 2491-2492, 1975 Pergamon Press.

Primary Examiner—Richard L. Raymond
Attorney, Agent, or Firm—Keil & Weinkauf

[57] ABSTRACT

Cyclohexenone derivatives of the formula

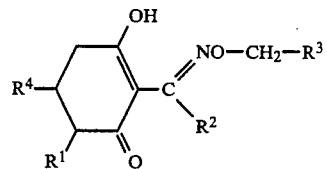

where $R^1$, $R^2$, $R^3$ and $R^4$ have the meanings stated in the description, herbicides which contain these compounds and a method for controlling undesirable plant growth.

10 Claims, No Drawings

CYCLOHEXENONE DERIVATIVES AND THEIR USE FOR CONTROLLING UNDESIRABLE PLANT GROWTH

The present invention relates to novel cyclohexenone derivatives, herbicides which contain these compounds and a method for controlling undesirable plant growth.

DE-A-3 121 355, DE-A-3 123 312 and DE-A-3 239 071 disclose a number of cyclohexenone derivatives which possess herbicidal activity.

We have found novel cyclohexenone derivatives of the formula I

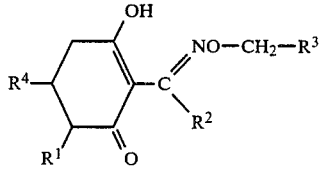

where $R^1$ is hydrogen or alkoxycarbonyl of 2 to 5 carbon atoms, $R^2$ is alkyl of 1 to 4 carbon atoms, $R^3$ is a 5-membered heterocyclic structure which contains 1 to 3 heteroatoms from the group consisting of N, O and S and may contain 1 or 2 double bonds and 1 or 2 substituents from the group consisting of $C_1$–$C_4$-alkyl, $C_1$–$C_4$-alkoxy, halogen, trifluoromethyl, $C_1$–$C_4$-alkoxymethyl, $C_1$–$C_4$-alkylthiomethyl, vinyl and phenyl, and $R^4$ is a 5-membered to 7-membered heterocyclic structure which contains one heteroatom or ring member, or two identical or different heteroatoms or ring members, from the group consisting of N, O, S, SO and $SO_2$, may contain 1, 2 or 3 double bonds and is unsubstituted or substituted by not more than 2 alkyl or alkoxy groups, each of 1 to 4 carbon atoms, or is a radical of the formula II

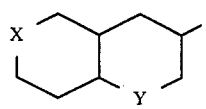

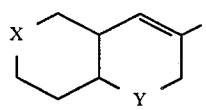

where X and Y are each N, O, S, SO or $SO_2$, and salts of these compounds.

The novel cyclohexenone derivatives have a particularly good action which in many cases is also species-specific.

The compounds of the formula I can occur in several tautomeric forms, all of which are embraced by the claim:

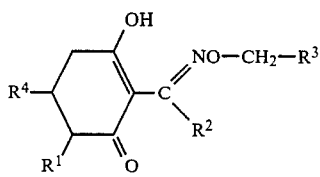

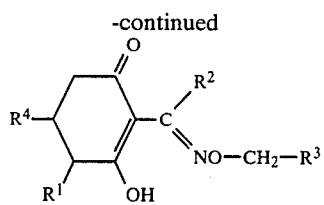

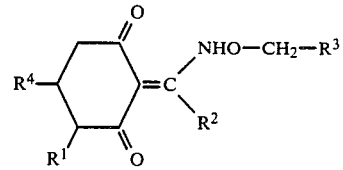

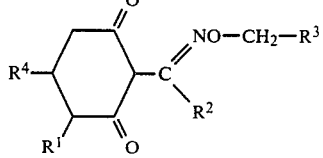

In formula I $R^1$ is hydrogen or alkoxycarbonyl of 1 to 4 carbon atoms, eg. methoxycarbonyl, ethoxycarbonyl, propoxycarbonyl or butoxycarbonyl, preferably methoxycarbonyl, in particular hydrogen, and $R^2$ is methyl, ethyl, n-propyl, isopropyl, n-butyl, sec.-butyl, isobutyl or tert.-butyl, the radicals of 2 or 3 carbon atoms being preferred.

$R^3$ is a 5-membered heterocyclic ring of 1 to 3 heteroatoms from the group consisting of N, O and S, with the exception of heterocyclic structures which possess more than two oxygen atoms or more than one sulfur atom in the ring. The heterocyclic rings may possess 1 or 2 double bonds and not more than 2 substituents, such as $C_1$–$C_4$-alkyl, $C_1$–$C_4$-alkoxy, halogen, trifluoromethyl, $C_1$–$C_4$-alkoxymethyl, $C_1$–$C_4$-alkylthiomethyl, vinyl or phenyl. Examples of substituents which give rise to particularly advantageous effects are furan-2-yl, tetrahydrofuran-2-yl, 1,3-dioxolan-2-yl, 2-phenyl-1,3-dioxolan-2-yl, 2,2-dimethyl-1,3-dioxolan-4-yl, 4,5-dimethyl-1,3-dioxolan-2-yl, 2-vinyl-1,3-dioxolan-4-yl, 3-phenyl-isoxazol-5-yl, 3-methyl-isoxazol-5-yl, 3-methoxymethyl-isoxazol-5-yl, 5-chlorothien-2-yl, 2-chlorothien-3-yl, 3,5-dichlorothien-2-yl, 2,5-dichlorothien-3-yl, 2,3-dichlorothien-4-yl, 2-chlorothien-4-yl, 2-isopropyl-1,3,4-oxadiazol-5-yl, 2-methyl-1,3,4-thiadiazol-5-yl, 5-chloro-1,2,3-thiadiazol-4-yl, thien-2-yl or thien-3-yl.

Particularly preferred radicals $R^3$ are thien-2-yl and thien-3-yl, each of which is unsubstituted or substituted by 1 or 2 chlorine atoms.

In formula I, $R^4$ is a 5-membered to 7-membered heterocyclic structure which contains 1 or 2 heteroatoms or ring members from the group consisting of N, O, S, SO and $SO_2$, may contain 1, 2 or 3 double bonds and is unsubstituted or substituted by not more than 2 alkyl or alkoxy groups, each of 1 to 4 carbon atoms, or is a radical of the formula II or of the formula (II)a

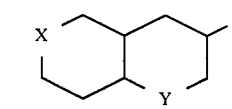

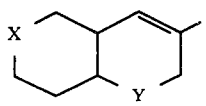

(IIa)

where X and Y are each N, O, S, SO or SO₂.

Typical examples of $R^4$ are 4-methyltetrahydropyran-3-yl, 3-methyltetrahydropyran-4-yl, 2-methyltetrahydropyran-4-yl, 2-methoxytetrahydropyran-4-yl, 3-methoxytetrahydropyran-4-yl, 2,6-dimethyltetrahydrothiopyran-3-yl, 1-oxo-tetrahydrothiopyran-3-yl, 1,1-dioxotetrahydrothiopyran-3-yl, 2-methyltetrahydrofuran-3-yl, 2,5-dimethyltetrahydrofuran-3-yl, 2-methoxymethyltetrahydrofuran-3-yl, tetrahydrothien-3-yl, 2,2-dimethyltetrahydrothien-3-yl, 2-methyl-1,3-dioxepan-5-yl, 2-isopropyl-1,3-dioxepan-5-yl, 4a,7,8,8a-tetrahydro-2H,5H-thiino[4,3-b]pyran-3-yl and 3,4,4a,7,8,8a-hexahydro-2H,5H-thiino-[4,3-b]pyran-3-yl. Preferred radicals $R^4$ are tetrahydropyran-3-yl, tetrahydropyran-4-yl, tetrahydrothiopyran-3-yl, tetrahydrothiopyran-4-yl, tetrahydrofuran-3-yl, tetrahydrothien-3-yl, pyrid-3-yl, 1,3-dioxepan-5-yl and the radicals 4a,7,8,8a-tetrahydro-2H,5H-pyrano[4,3-b]pyran-3-yl, 3,4,4a,7,8,8a-hexahydro-2H,5H-pyrano[4,3-b]pyran-3-yl, 4a,7,8,8a-tetrahydro-2H,5H-thiino[4,3-b]-thiin-3-yl and 3,4,4a,7,8,8a-hexahydro-2H,5H-thiino[4,3-b]thiin-3-yl which are defined by the formulae II and IIa.

Suitable salts of the compounds of the formula I are those which can be used in agriculture, for example the alkali metal salts, in particular the potassium and sodium salts, the alkaline earth metal salts, in particular the calcium, magnesium and barium salts, manganese salts, copper salts, zinc salts and iron salts, as well as ammonium, phosphonium, sulfonium and sulfoxonium salts, eg. ammonium, tetraalkylammonium, benzyltrialkylammonium, trialkylsulfonium and trialkylsulfoxonium salts.

The cyclohexenone derivatives of the formula I can be obtained by reacting a tricarbonyl compound of the formula III

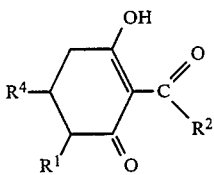

(III)

where $R^1$, $R^2$ and $R^4$ have the above meanings, with an ammonium compound of the formula $R^3$—CH₂O—NH₃Y, where Y is an anion (eq. chloride, bromide or sulfate). To do this, the two reactants in a solvent are reacted in the presence of a base at an adequate temperature, eg. from 0° to 80° C., in the presence or absence of water. Examples of suitable bases are carbonates, bicarbonates, acetates, alcoholates, oxides and hydroxides of alkali metals and alkaline earth metals, in particular of sodium, potassium, magnesium and calcium, and organic bases, such as pyridine or tertiary amines, eg. triethylamine.

Examples of solvents are dimethyl sulfoxide, alcohols, such as methanol, ethanol, or isopropanol, benzene, toluene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, partitioning the residue between methylene chloride and water, and distilling off the solvent under reduced pressure.

The compounds of the formula I can also be obtained by reacting a tricarbonyl compound of the formula III with an appropriate alkoxyamine of the formula $R^3$—CH₂O—NH₂ in a suitable solvent, a suitable reaction temperature being in general from 15° to 70° C. The alkoxyamine may also be used in the form of an aqueous solution; depending on the solvent used for the other reactant, a single-phase or two-phase reaction mixture is obtained.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

Alkali metal salts of the compounds of the formula I can be obtained by treating these compounds with sodium hydroxide, potassium hydroxide or a sodium or potassium alcoholate in aqueous solution or in an organic solvent, such as methanol, ethanol, acetone or toluene.

Other metal salts, eg. the manganese, copper, zinc, iron, calcium, magnesium and barium salts, can be prepared from the sodium salts in a conventional manner, and ammonium and phosphonium salts can be obtained using ammonia or phosphonium, sulfonium or sulfoxonium hydroxides.

The tricarbonyl compounds of the formula III are in general known. They can be prepared, for example, from the corresponding cyclohexane-1,3-diones (IV) or (Iva) or (Ivb)

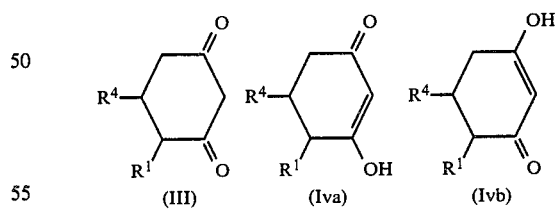

in a conventional manner (Tetrahedron Lett. 29 (1975), 2491).

They may therefore also be prepared via the enol ester intermediates, which are obtained, possibly as isomer mixtures, in the acylation of compounds (IV) and undergo rearrangement in the presence of an imidazole or pyridine derivative (JP-A-63 052/1979).

The compounds of the formula (IV) are also obtained by a conventional method, as shown in the scheme below:

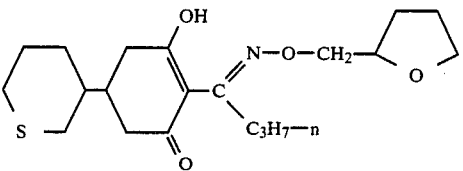

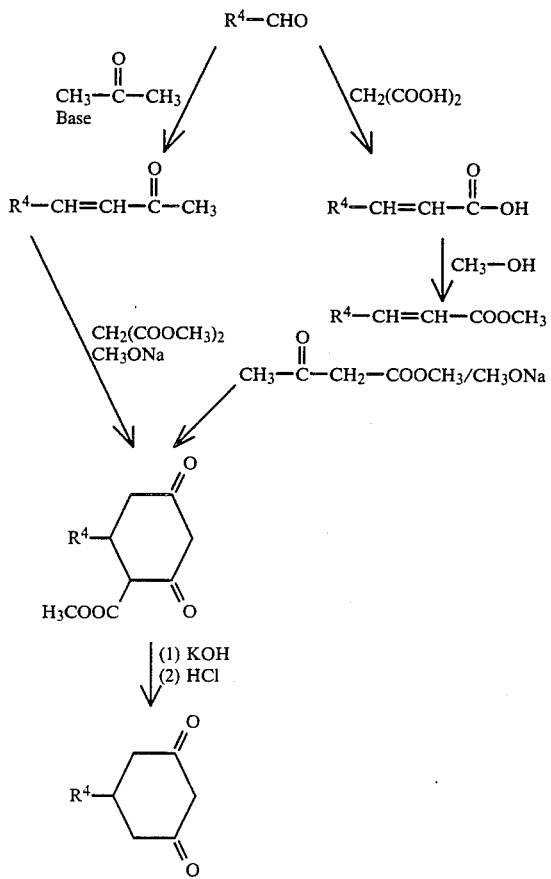

The Example which follows illustrates the preparation of the cyclohexenone derivatives of the formula I.

EXAMPLE 2.82 g (10 millimoles) of 2-butyryl-3-hydroxy-5-(tetrahydrothiopyran-3-yl)-cyclohex-2-en-1-one was stirred together with 1.69 g (11 millimoles) of tetrahydrofur-2-ylmethoxyamine hydrochloride and 0.93 g (11 millimoles) of sodium bicarbonate in 20 ml of methanol for 12 hours at 25° C. The mixture was evaporated down, the residue was taken up with dichlorbmethane and the solution was extracted by shaking with water. The dried dichloromethane solution was evaporated down to give 3.1 g (8.1 millimoles) of 3-hydroxy-2-(1-tetrahydrofur-2-ylmethoxyiminobutyl)-5-(tetrahydrothiopyran-3-yl)-cyclohex-2-en-1-one as a viscous oil.

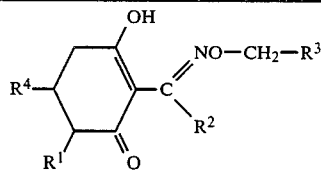

Calculated: C: 62.96, H: 8.19, N: 3.67, Found: C: 63.0, H: 7.9, N: 4.1.

Other cyclohexenones according to the invention are listed in the Table below, where A is fur-2-yl,
B is tetrahydrofuran-2-yl,
C is 1,3-dioxolan-2-yl,
D is 2-phenyl-1,3-dioxolan-2-yl,
E is 2,2-dimethyl-1,3-dioxolan-4-yl,
F is 4,5-dimethyl-1,3-dioxolan-2-yl,
G is 2-vinyl-1,3-dioxolan-4-yl,
H is 3-phenyl-isoxazol-5-yl,
I is 3-methyl-isoxazol-5-yl,
K is 3-methoxymethyl-isoxazol-5-yl,
L is 5-chlorothien-2-yl,
M is 2-chlorothien-3-yl,
N is 3,5-dichlorothien-2-yl,
O is 2,5-dichlorothien-3-yl,
P is 2,3-dichlorothien-4-yl,
Q is 2-chlorothien-4-yl,
R is 2-isopropyl-1,3,4-oxadiazol-5-yl,
S is 2-methyl-1,3,4-thiadiazol-5-yl,
T is 5-chloro-1,2,3-thiadiazol-4-yl,
U is thien-2-yl,
V is thien-3-yl,
W is 5-bromothien-2-yl,
X is 4-bromothien-2-yl and
Y is 5-bromothien-3-yl.

$^1$H-NMR spectra were measured in CDCl$_3$, using TMS as the internal standard. In the Tables, s=singlet, d=doublet, t=triplet, q=quartet and m=multiplet.

| No. | R$^4$ | R$^1$ | R$^2$ | R$^3$ | Characteristic signals $^1$H—NMR (ppm) |
|---|---|---|---|---|---|
| 1 | tetrahydropyran-3-yl | COOCH$_3$ | n-C$_3$H$_7$ | L | |
| 2 | tetrahydropyran-3-yl | H | n-C$_3$H$_7$ | B | 0.96(3H,t); 1.2–2.8(16H); 2.88(2H,t); 3.25(2H, m); 3.7–4.3(7H) |
| 3 | tetrahydropyran-3-yl | H | C$_2$H$_5$ | L | |
| 4 | tetrahydropyran-3-yl | H | n-C$_3$H$_7$ | U | 3.9 (t); 5.2 (s); 7.35 (m) |
| 5 | tetrahydropyran-3-yl | H | n-C$_3$H$_7$ | L | 0.9 (t); 3.9 (t); 5.1 (s) |
| 6 | tetrahydropyran-3-yl | H | n-C$_3$H$_7$ | P | 0.95 (t); 5.0 (s); 7.2 (s) |
| 7 | tetrahydropyran-4-yl | COOCH$_3$ | n-C$_3$H$_7$ | L | |
| 8 | tetrahydropyran-4-yl | COOCH$_3$ | n-C$_3$H$_7$ | M | |
| 9 | tetrahydropyran-4-yl | H | n-C$_3$H$_7$ | V | 2.25 (t); 5.1 (s); 7.1 (m) |
| 10 | tetrahydropyran-4-yl | H | n-C$_3$H$_7$ | L | 2.9 (q); 5.1 (s); 6.8 (m) |
| 11 | tetrahydropyran-4-yl | H | n-C$_3$H$_7$ | M | |
| 12 | tetrahydropyran-4-yl | H | n-C$_3$H$_7$ | N | |
| 13 | tetrahydropyran-4-yl | H | n-C$_3$H$_7$ | O | |

-continued

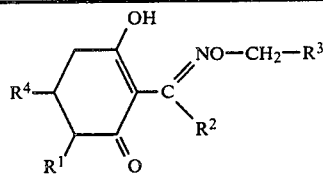

| No. | R⁴ | R¹ | R² | R³ | Characteristic signals ¹H—NMR (ppm) |
|---|---|---|---|---|---|
| 14 | tetrahydropyran-4-yl | H | n-C₃H₇ | P | 3.35 (t); 4.0 (d); 4.9 (s) |
| 15 | tetrahydropyran-4-yl | H | n-C₃H₇ | Q | 3.35 (t); 4.0 (d); 6.9 (s) |
| 16 | tetrahydropyran-4-yl | H | C₂H₅ | U | 3.4 (t); 5.2 (s); 7.3 (m) |
| 17 | tetrahydropyran-4-yl | H | C₂H₅ | B | 1.1 (t); 1.6 (d); 3.4 (t) |
| 18 | tetrahydropyran-4-yl | H | C₂H₅ | C | |
| 19 | tetrahydropyran-4-yl | H | C₂H₅ | D | |
| 20 | tetrahydropyran-4-yl | H | C₂H₅ | E | |
| 21 | tetrahydropyran-4-yl | H | C₂H₅ | F | |
| 22 | tetrahydropyran-4-yl | H | C₂H₅ | G | |
| 23 | tetrahydropyran-4-yl | H | C₂H₅ | V | 2.9 (q); 5.1 (s); 7.1 (d) |
| 24 | tetrahydropyran-4-yl | H | C₂H₅ | I | 1.1 (t); 2.3 (t); 5.1 (s); 6.1 (s) |
| 25 | tetrahydropyran-4-yl | H | C₂H₅ | K | |
| 26 | tetrahydropyran-4-yl | H | C₂H₅ | L | 1.65 (d); 3.3 (t); 5.1 (s) |
| 27 | tetrahydropyran-4-yl | H | C₂H₅ | M | |
| 28 | tetrahydropyran-4-yl | H | C₂H₅ | N | |
| 29 | tetrahydropyran-4-yl | H | C₂H₅ | O | |
| 30 | tetrahydropyran-4-yl | H | C₂H₅ | P | |
| 31 | tetrahydropyran-4-yl | H | C₂H₅ | Q | 3.4 (t); 4.9 (s); 6.9 (s) |
| 32 | tetrahydropyran-4-yl | H | C₂H₅ | R | |
| 33 | tetrahydropyran-4-yl | H | C₂H₅ | S | |
| 34 | tetrahydropyran-4-yl | H | C₂H₅ | T | |
| 35 | 4-methyltetrahydropyran-3-yl | H | n-C₃H₇ | L | 0.95(t); 1.5(q); 2.85(t); 3.2(t); 3.4(t); 5.1(s) |
| 36 | 4-methyltetrahydropyran-3-yl | H | n-C₃H₇ | I | 0.94(3H,t); 0.98(3H,d); 2.31(3H,s); 2.84(2H,t); 5.09(2H,s); 6.16(1H,s) |
| 37 | 4-methyltetrahydropyran-3-yl | H | C₂H₅ | L | |
| 38 | 4-methyltetrahydropyran-3-yl | H | C₂H₅ | M | |
| 39 | 3-methyltetrahydropyran-4-yl | H | C₂H₅ | L | |
| 40 | 3-methyltetrahydropyran-4-yl | H | C₂H₅ | M | |
| 41 | 3-methyltetrahydropyran-4-yl | H | n-C₃H₇ | L | |
| 42 | 3-methyltetrahydropyran-4-yl | H | n-C₃H₇ | M | |
| 43 | 2-methyltetrahydropyran-4-yl | H | n-C₃H₇ | L | |
| 44 | 2-methyltetrahydropyran-4-yl | H | n-C₃H₇ | M | |
| 45 | 2-methyltetrahydropyran-4-yl | H | n-C₃H₇ | N | |
| 46 | 2-methyltetrahydropyran-4-yl | H | n-C₃H₇ | E | |
| 47 | 2-methyltetrahydropyran-4-yl | H | n-C₃H₇ | T | |
| 48 | 2-methoxytetrahydropyran-4-yl | H | n-C₃H₇ | T | |
| 49 | 2-methoxytetrahydropyran-4-yl | H | n-C₃H₇ | L | |
| 50 | 2-methoxytetrahydropyran-4-yl | H | n-C₃H₇ | M | |
| 51 | 3-methoxytetrahydropyran-4-yl | H | n-C₃H₇ | L | |
| 52 | 3-methoxytetrahydropyran-4-yl | H | n-C₃H₇ | M | |
| 53 | tetrahydrothiopyran-3-yl | H | n-C₃H₇ | U | 2.6 (m); 3.0 (t); 5.2 (s) |
| 54 | tetrahydrothiopyran-3-yl | H | n-C₃H₇ | B | 0.96(3H,t); 1.2–2.7(20H); 2.88(2H,t); 3.84(2H,m); 4.09(3H) |
| 55 | tetrahydrothiopyran-3-yl | H | n-C₃H₇ | C | |
| 56 | tetrahydrothiopyran-3-yl | H | n-C₃H₇ | D | |
| 57 | tetrahydrothiopyran-3-yl | H | n-C₃H₇ | E | |
| 58 | tetrahydrothiopyran-3-yl | H | n-C₃H₇ | F | |
| 59 | tetrahydrothiopyran-3-yl | H | n-C₃H₇ | G | |
| 60 | tetrahydrothiopyran-3-yl | H | n-C₃H₇ | H | 0.88(t); 5.19(s); 6.72(s); 7.42(m); 7.8(m) |
| 61 | tetrahydrothiopyran-3-yl | H | n-C₃H₇ | I | 0.94(3H,t); 2.31(3H,s); 2.84(2H,t); 3.00(1H,t); 5.09(2H,s); 6.16(1H,s) |
| 62 | tetrahydrothiopyran-3-yl | H | n-C₃H₇ | V | 0.85 (t); 4.93 (s); 6.92 (s); 7.07 (s) |
| 63 | tetrahydrothiopyran-3-yl | H | n-C₃H₇ | L | 0.96(3H,t); 2.84(2H,t); 3.01(1H,t); 5.06(2H,s); 6.79(2H) |
| 64 | tetrahydrothiopyran-3-yl | H | n-C₃H₇ | M | |
| 65 | tetrahydrothiopyran-3-yl | H | n-C₃H₇ | N | |
| 66 | tetrahydrothiopyran-3-yl | H | n-C₃H₇ | O | 0.87 (t); 4.93 (s); 6.98 (s) |
| 67 | tetrahydrothiopyran-3-yl | H | n-C₃H₇ | P | 0.92 (t); 4.98 (s); 7.23 (s) |
| 68 | tetrahydrothiopyran-3-yl | H | n-C₃H₇ | Q | 0.85 (t); 4.93 (s); 6.92 (s); 7.06 (s) |
| 69 | tetrahydrothiopyran-3-yl | H | n-C₃H₇ | R | |
| 70 | tetrahydrothiopyran-3-yl | H | n-C₃H₇ | S | |
| 71 | tetrahydrothiopyran-3-yl | H | n-C₃H₇ | T | |
| 72 | tetrahydrothiopyran-4-yl | H | n-C₃H₇ | L | |
| 73 | tetrahydrothiopyran-4-yl | H | n-C₃H₇ | M | |
| 74 | tetrahydrothiopyran-4-yl | H | n-C₃H₇ | N | |
| 75 | tetrahydrothiopyran-4-yl | H | n-C₃H₇ | O | |
| 76 | 2,6-dimethyltetrahydrothiopyran-3-yl | H | n-C₃H₇ | A | |
| 77 | 2,6-dimethyltetrahydrothiopyran-3-yl | H | n-C₃H₇ | B | |
| 78 | 2,6-dimethyltetrahydrothiopyran-3-yl | H | n-C₃H₇ | C | |
| 79 | 1-oxo-tetrahydrothiopyran-3-yl | H | n-C₃H₇ | C | |
| 80 | 1-oxo-tetrahydrothiopyran-3-yl | H | n-C₃H₇ | E | |
| 81 | 1-oxo-tetrahydrothiopyran-3-yl | H | n-C₃H₇ | L | 0.96 (t); 3.5 (m); 5.07 (s); 6.83 (m) |

-continued

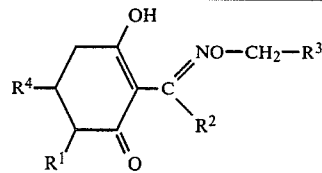

| No. | R⁴ | R¹ | R² | R³ | Characteristic signals ¹H—NMR (ppm) |
|---|---|---|---|---|---|
| 82 | 1-oxo-tetrahydrothiopyran-3-yl | H | n-C₃H₇ | M | |
| 83 | 1,1-dioxo-tetrahydrothiopyran-3-yl | H | n-C₃H₇ | C | |
| 84 | 1,1-dioxo-tetrahydrothiopyran-3-yl | H | n-C₃H₇ | E | |
| 85 | 1,1-dioxo-tetrahydrothiopyran-3-yl | H | n-C₃H₇ | L | 0.95(t); 3.07(m); 5.09(s); 6.80(d); 6.88(d) |
| 86 | 1,1-dioxo-tetrahydrothiopyran-3-yl | H | n-C₃H₇ | M | |
| 87 | tetrahydrofuran-3-yl | H | n-C₃H₇ | P | 0.94 (t); 3.43 (t); 4.98 (s); 7.18 (s) |
| 88 | tetrahydrofuran-3-yl | H | n-C₃H₇ | Q | 0.96(t); 2.88(t); 3.42(t); 4.92(s); 6.9(s); 7.05(s) |
| 89 | tetrahydrofuran-3-yl | H | n-C₃H₇ | L | 0.94 (t); 5.07 (s); 6.82 (d); 6.88 (d) |
| 90 | tetrahydrofuran-3-yl | H | n-C₃H₇ | M | |
| 91 | 2-methyltetrahydrofuran-3-yl | H | n-C₃H₇ | L | 0.95 (t); 1.28 (d); 5.08 (s); 6.81 (d); 6.87 (d) |
| 92 | 2-methyltetrahydrofuran-3-yl | H | n-C₃H₇ | M | |
| 93 | 2,5-dimethyltetrahydrofuran-3-yl | H | n-C₃H₇ | M | |
| 94 | 2,5-dimethyltetrahydrofuran-3-yl | H | n-C₃H₇ | L | |
| 95 | 2-methoxymethyltetrahydrofuran-3-yl | H | n-C₃H₇ | L | |
| 96 | 2-methoxymethyltetrahydrofuran-3-yl | H | n-C₃H₇ | M | |
| 97 | tetrahydrothien-3-yl | H | n-C₃H₇ | P | 0.95 (t); 4.97 (s); 7.18 (s) |
| 98 | tetrahydrothien-3-yl | H | n-C₃H₇ | Q | 0.95 (t); 4.94 (s); 6.88 (s); 7.03 (s) |
| 99 | tetrahydrothien-3-yl | H | n-C₃H₇ | L | |
| 100 | tetrahydrothien-3-yl | H | n-C₃H₇ | M | |
| 101 | tetrahydrothien-3-yl | H | C₂H₅ | U | 1.10(t); 5.22(s); 7.03(m); 7.10(d); 7.35(d) |
| 102 | tetrahydrothien-3-yl | H | C₂H₅ | V | 1.11 (t); 5.05 (s); 7.09 (d); 7.34 (m) |
| 103 | tetrahydrothien-3-yl | H | C₂H₅ | L | |
| 104 | tetrahydrothien-3-yl | H | C₂H₅ | M | |
| 105 | tetrahydrothien-3-yl | H | C₂H₅ | N | |
| 106 | 2,2-dimethyltetrahydrothien-3-yl | H | n-C₃H₇ | E | |
| 107 | 2,2-dimethyltetrahydrothien-3-yl | H | n-C₃H₇ | I | 0.94(t); 1.34(s); 1.50(s); 5.09(s); 6.15(s) |
| 108 | 2,2-dimethyltetrahydrothien-3-yl | H | n-C₃H₇ | L | |
| 109 | 2,2-dimethyltetrahydrothien-3-yl | H | n-C₃H₇ | M | |
| 110 | 2,2-dimethyltetrahydrothien-3-yl | H | C₂H₅ | E | |
| 111 | 2,2-dimethyltetrahydrothien-3-yl | H | C₂H₅ | I | 1.12(t); 1.33(s); 1.49(s); 5.10(s); 6.15(s) |
| 112 | 2,2-dimethyltetrahydrothien-3-yl | H | C₂H₅ | L | |
| 113 | 2,2-dimethyltetrahydrothien-3-yl | H | C₂H₅ | M | |
| 114 | 3-pyridyl | H | C₂H₅ | P | 1.14(t); 2.73(m); 2.9(q); 3.4(m); 5,0(s) |
| 115 | 3-pyridyl | H | C₂H₅ | I | 1.14(t); 2.3(s); 2.9(q); 3.4(m); 5.1(s); 6.18(s) |
| 116 | 3-pyridyl | H | C₂H₅ | L | 1.16 (t); 2.9 (q); 5.1 (s) |
| 117 | 3-pyridyl | H | C₂H₅ | M | |
| 118 | 3-pyridyl | H | n-C₃H₇ | Q | 0.95 (t); 1.55 (q); 2.9 (t); 4.95 (s) |
| 119 | 3-pyridyl | H | n-C₃H₇ | I | 1.00(3H,t); 2.31(3H,s); 3.63(1H,m); 6.02(1H,s); 7.25(1H,m); 7.58(1H,m); 8.50(2H,m) |
| 120 | 3-pyridyl | H | n-C₃H₇ | L | 0.95 (t); 1.55 (q); 5.1 (s) |
| 121 | 1,3-dioxepan-5-yl | H | n-C₃H₇ | L | |
| 122 | 2-methyl-1,3-dioxepan-5-yl | H | n-C₃H₇ | L | |
| 123 | 2-isopropyl-1,3-dioxepan-5-yl | H | C₂H₅ | U | |
| 124 | 2-isopropyl-1,3-dioxepan-5-yl | H | C₂H₅ | B | |
| 125 | 2-isopropyl-1,3-dioxepan-5-yl | H | C₂H₅ | C | |
| 126 | 2-isopropyl-1,3-dioxepan-5-yl | H | C₂H₅ | D | |
| 127 | 2-isopropyl-1,3-dioxepan-5-yl | H | C₂H₅ | E | |
| 128 | 2-isopropyl-1,3-dioxepan-5-yl | H | C₂H₅ | F | |
| 129 | 2-isopropyl-1,3-dioxepan-5-yl | H | C₂H₅ | G | |
| 130 | 2-isopropyl-1,3-dioxepan-5-yl | H | C₂H₅ | V | |
| 131 | 2-isopropyl-1,3-dioxepan-5-yl | H | C₂H₅ | I | 0.9 (m); 2.3 (s); 5.1 (s) |
| 132 | 2-isopropyl-1,3-dioxepan-5-yl | H | C₂H₅ | K | |
| 133 | 2-isopropyl-1,3-dioxepan-5-yl | H | C₂H₅ | L | 0.9 (m); 2.9 (m); 5.1 (s) |
| 134 | 2-isopropyl-1,3-dioxepan-5-yl | H | C₂H₅ | M | |
| 135 | 2-isopropyl-1,3-dioxepan-5-yl | H | C₂H₅ | N | |
| 136 | 2-isopropyl-1,3-dioxepan-5-yl | H | C₂H₅ | O | |
| 137 | 2-isopropyl-1,3-dioxepan-5-yl | H | C₂H₅ | P | |
| 138 | 2-isopropyl-1,3-dioxepan-5-yl | H | C₂H₅ | Q | 1.1 (t); 2.9 (q); 4.9 (s) |
| 139 | 2-isopropyl-1,3-dioxepan-5-yl | H | C₂H₅ | R | |
| 140 | 2-isopropyl-1,3-dioxepan-5-yl | H | C₂H₅ | S | |
| 141 | 2-isopropyl-1,3-dioxepan-5-yl | H | C₂H₅ | T | |
| 142 | 4a,7,8,8a-tetrahydro-2H,5H—pyrano[4,3-b]pyran-3-yl | H | n-C₃H₇ | A | |
| 143 | 4a,7,8,8a-tetrahydro-2H,5H—pyrano[4,3-b]pyran-3-yl | H | n-C₃H₇ | B | 0.98 (t); 4.1 (m); 4.2 (s); 5.3 (s) |
| 144 | 4a,7,8,8a-tetrahydro-2H,5H—pyrano[4,3-b]pyran-3-yl | H | n-C₃H₇ | C | |
| 145 | 4a,7,8,8a-tetrahydro-2H,5H—pyrano[4,3-b]pyran-3-yl | H | n-C₃H₇ | D | |
| 146 | 4a,7,8,8a-tetrahydro-2H,5H—pyrano[4,3-b]pyran-3-yl | H | n-C₃H₇ | E | |
| 147 | 4a,7,8,8a-tetrahydro-2H,5H—pyrano[4,3-b]pyran-3-yl | H | n-C₃H₇ | F | |
| 148 | 4a,7,8,8a-tetrahydro-2H,5H—pyrano[4,3-b]pyran-3-yl | H | n-C₃H₇ | G | |
| 149 | 4a,7,8,8a-tetrahydro-2H,5H—pyrano[4,3-b]pyran-3-yl | H | n-C₃H₇ | H | |
| 150 | 4a,7,8,8a-tetrahydro-2H,5H—pyrano[4,3-b]pyran-3-yl | H | n-C₃H₇ | I | 0.9(t); 2.3(s); 5.1(s); 5.35(s); 6.15(s) |
| 151 | 4a,7,8,8a-tetrahydro-2H,5H—pyrano[4,3-b]pyran-3-yl | H | n-C₃H₇ | U | 0.92(t); 5.2(s); 7.0(m); 7.1(d); 7.35(d) |
| 152 | 4a,7,8,8a-tetrahydro-2H,5H—pyrano[4,3-b]pyran-3-yl | H | n-C₃H₇ | L | 0.92(t); 4.2(s); 5.08(s); 5.3(s); 6.82(m) |

-continued

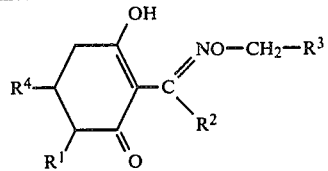

| No. | R⁴ | R¹ | R² | R³ | Characteristic signals ¹H—NMR (ppm) |
|---|---|---|---|---|---|
| 153 | 4a,7,8,8a-tetrahydro-2H,5H—pyrano[4,3-b]pyran-3-yl | H | n-C₃H₇ | M | |
| 154 | 4a,7,8,8a-tetrahydro-2H,5H—pyrano[4,3-b]pyran-3-yl | H | n-C₃H₇ | V | 0.95(t); 5.03(s); 5.3(s); 7.05(d); 7.3(m) |
| 155 | 4a,7,8,8a-tetrahydro-2H,5H—pyrano[4,3-b]pyran-3-yl | H | n-C₃H₇ | O | |
| 156 | 4a,7,8,8a-tetrahydro-2H,5H—pyrano[4,3-b]pyran-3-yl | H | n-C₃H₇ | P | 0.93(t); 4.98(s); 5.35(s); 7.18(s) |
| 157 | 4a,7,8,8a-tetrahydro-2H,5H—pyrano[4,3-b]pyran-3-yl | H | n-C₃H₇ | Q | 0.93(t); 4.96(s); 5.35(s); 6.9(s); 7.05(s) |
| 158 | 4a,7,8,8a-tetrahydro-2H,5H—pyrano[4,3-b]pyran-3-yl | H | n-C₃H₇ | R | |
| 159 | 4a,7,8,8a-tetrahydro-2H,5H—pyrano[4,3-b]pyran-3-yl | H | n-C₃H₇ | S | |
| 160 | 4a,7,8,8a-tetrahydro-2H,5H—pyrano[4,3-b]pyran-3-yl | H | n-C₃H₇ | T | |
| 161 | 3,4,4a,7,8,8a-hexahydro-2H,5H—pyrano[4,3-b]pyran-3-yl | H | n-C₃H₇ | L | 0.92(t); 4.05(m); 5.08(s); 6.82(m) |
| 162 | 3,4,4a,7,8,8a-hexahydro-2H,5H—pyrano[4,3-b]pyran-3-yl | H | n-C₃H₇ | M | |
| 163 | 4a,7,8,8a-tetrahydro-2H,5H—thiino[4,3-b]pyran-3-yl | H | n-C₃H₇ | L | |
| 164 | 4a,7,8,8a-tetrahydro-2H,5H—thiino[4,3-b]pyran-3-yl | H | n-C₃H₇ | M | |
| 165 | 4a,7,8,8a-tetrahydro-2H,5H—thiino[4,3-b]pyran-3-yl | H | n-C₃H₇ | N | |
| 166 | 3,4,4a,7,8,8a-hexahydro-2H,5H—thiino[4,3-b]pyran-3-yl | H | n-C₃H₇ | L | |
| 167 | 3,4,4a,7,8,8a-hexahydro-2H,5H—thiino[4,3-b]pyran-3-yl | H | n-C₃H₇ | M | |
| 168 | 4a,7,8,8a-tetrahydro-2H,5H—thiino[4,3-b]thiin-3-yl | H | n-C₃H₇ | L | |
| 169 | 4a,7,8,8a-tetrahydro-2H,5H—thiino[4,3-b]thiin-3-yl | H | n-C₃H₇ | M | |
| 170 | 4a,7,8,8a-tetrahydro-2H,5H—thiino[4,3-b]thiin-3-yl | H | n-C₃H₇ | N | |
| 171 | 4a,7,8,8a-tetrahydro-2H,5H—thiino[4,3-b]thiin-3-yl | H | n-C₃H₇ | O | |
| 172 | 4a,7,8,8a-tetrahydro-2H,5H—thiino[4,3-b]thiin-3-yl | H | C₂H₅ | L | |
| 173 | 4a,7,8,8a-tetrahydro-2H,5H—thiino[4,3-b]thiin-3-yl | H | C₂H₅ | M | |
| 174 | 4a,7,8,8a-tetrahydro-2H,5H—thiino[4,3-b]thiin-3-yl | H | C₂H₅ | N | |
| 175 | 3,4,4a,7,8,8a-hexahydro-2H,5H—thiino[4,3-b]thiin-3-yl | H | n-C₃H₇ | L | |
| 176 | 3,4,4a,7,8,8a-hexahydro-2H,5H—thiino[4,3-b]thiin-3-yl | H | n-C₃H₇ | M | |
| 177 | 3,4,4a,7,8,8a-hexahydro-2H,5H—thiino[4,3-b]thiin-3-yl | H | n-C₃H₇ | N | |
| 178 | 3,4,4a,7,8,8a-hexahydro-2H,5H—thiino[4,3-b]thiin-3-yl | H | C₂H₅ | L | |
| 179 | 3,4,4a,7,8,8a-hexahydro-2H,5H—thiino[4,3-b]thiin-3-yl | H | C₂H₅ | M | |
| 180 | 3,4,4a,7,8,8a-hexahydro-2H,5H—thiino[4,3-b]thiin-3-yl | H | C₂H₅ | N | |
| 181 | 4a,7,8,8a-tetrahydro-2H,5H—pyrano[4,3-b]pyran-3-yl | H | n-C₃H₇ | K | 0.92(t); 3.4(s); 4.55(s) 5.15(s); 5.35(s); 6.4(s) |
| 182 | tetrahydropyran-3-yl | H | n-C₃H₇ | Q | 0.95(t); 4.9(s); 6.9(s); 7.05(s) |
| 183 | tetrahydropyran-3-yl | H | CH₃ | U | 2.3(s); 3.2(t); 5.2(s) |
| 184 | tetrahydrothiopyran-3-yl | H | n-C₃H₇ | W | 0.92(t); 5.09(s); 6.83(d); 6.94(d) |
| 185 | tetrahydrothiopyran-3-yl | H | n-C₃H₇ | X | 0.83(t); 5.18(s); 7.11(s); 7.63(s) |
| 186 | tetrahydrothiopyran-3-yl | H | n-C₃H₇ | Y | 0.95(t); 4.96(s); 7.03(s); 7.17(s) |
| 187 | tetrahydropyran-3-yl | H | CH₃ | U | 0.95(t); 3.9(t); 6.9(s) |
| 188 | tetrahydropyran-3-yl | H | n-C₃H₇ | Q | 2.3(s); 3.15(t); 5.2(s) |
| 189 | 3-methoxymethylisoxazol-5-yl | H | n-C₃H₇ | V | 0.95(t); 3.4(s); 4.48(s); 4.95(s) |
| 190 | 3-methoxymethylisoxazol-5-yl | H | n-C₃H₇ | Q | 0.95(t); 3.4(s); 4.48(s); 5.05(s); 6.1(s); |
| 191 | 3-methoxymethylisoxazol-5-yl | H | n-C₃H₇ | I | 0.92(t); 2.34(s); 3.4(s); 4.5(s); 5.1(s); 6.3(s); 6.34(s) |

The cyclohexenone derivatives of the formula I are remarkably good herbicidal active ingredients particularly on Gramineae species. They are well tolerated and are thus selective in broadleaved crops.

The compounds may be applied as herbicides for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound 61 is mixed with 10 parts by weight of N-methyl-alpha-pyrrolidone. A mixture is obtained which is suitable for application in the form of very fine drops.

II. 10 parts by weight of compound 61 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salts of dodecylbenzenesulfonic acid, and 2 parts by weight of the adduct of 40 moles of ethylene oxide and 1 mole of castor oil.

III. 20 parts by weight of compound 36 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound 63 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. 80 parts by weight of compound 63 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound 36 is intimately mixed with 95 parts by weight of particulate kaolin. A dust is obtained containing 5% by weight of the active ingredient.

VII. 30 parts by weight of compound 63 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 61 is intimately mixed with 10 parts of the sodium salt of a phenolsulfonic acid-urea-formaldehyde condensate, 2 parts of silica gel and 48 parts of water to give a stable aqueous dispersion.

IX. 20 parts of compound 36 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.05 to 5 kg/ha, but is preferably from 0.1 to 3 kg/ha.

The action of the cyclohexenone derivatives of the formula I on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For The preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment were 0.25, 0.5 and 3.0 kg of active ingredient per hectare. No covers were placed on the vessels in this method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Avena sativa, Echinochloa crus-galli, Lolium multiflorum, Mentha piperita, Sinapis alba, Medicago sativa, Hordeum vulgare, Zea mays, Avena fatua* and *Setaria italica*.

On preemergence application, compounds nos. 61 and 36 proved to be herbicidally effective on plants from the grasses family, whereas *Sinapis alba*, as a representative of dicotyledonous plants, remained completely undamaged.

On postemergence application, various grasses were excellently controlled by compounds nos. 61 and 36; no symptoms of damage were evident on Mentha piperita.

In *Medicago sativa*, unwanted grassy vegetation, including volunteer crops, can be combatted with compounds nos 61 and 63 without causing damage to the crop plant.

In view of the spectrum of weeds which can be combatted, the tolerance of the active ingredients according to the invention by crop plants, the desired influence on the growth of crop plants, and in view of the numerous application methods possible, the cyclohexenone derivatives of the formula I may be used in a large number of crop plants.

The following may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus spp.* | apple trees |
| *Manihot esculenta* | cassava |
| *Medicago sativa* | alfalfa (lucerne) |
| *Mentha piperita* | peppermint |
| *Musa spp.* | banana plants |
| *Nicothiana tabacum* | tobacco |
| (*N. rustica*) | |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus spp.* | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the novel active ingredients may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the compounds of the formula I, or herbicidal agents containing them, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

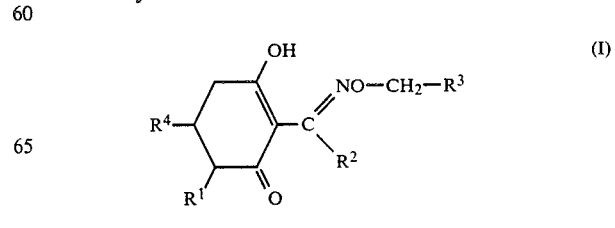

where $R^1$ is hydrogen or alkoxycarbonyl of 2 to 5 carbon atoms, $R^2$ is alkyl of 1 to 4 carbon atoms, $R^3$ is a 5-membered heterocyclic structure which contains 1 to 3 heteroatoms from the group consisting of N, O and S, with the exception of heterocyclic structures which possess more than two oxygen atoms or more than one sulfur atom in the ring, and may contain 1 to 2 double bonds and 1 or 2 substituents from the group consisting of $C_1$–$C_4$-alkyl, $C_1$–$C_4$-alkoxy, halogen, trifluoromethyl, $C_1$–$C_4$-alkoxymethyl, $C_1$–$C_4$-alkylthiomethyl, vinyl and phenyl, and $R^4$ is a 5-membered to 7-membered heterocyclic structure which contains one or two identical or different heteroatoms as ring members, from the group consisting of N, O, S, SO and $SO_2$, may contain 1, 2 or 3 double bonds and is unsubstituted or substituted by not more than 2 alkyl, or alkoxy groups, each of 1 to 4 carbon atoms, or is a radical of the formula II

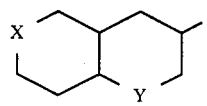
(II)

or IIa

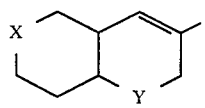
(IIa)

where X and Y are each N, O, S, SO or $SO_2$, or a salt thereof.

2. A cyclohexenone derivative of the formula I as set forth in claim 1, where $R^3$ is a substituent selected from the group consisting of furan-2-yl, tetrahydro-furan-2-yl, 1,3-dioxolan-2-yl, 2-phenyl-1,3-dioxolan-2-yl, 2,2-dimethyl-1,3-dioxolan-4-yl, 4,5-dimethyl-1,3-dioxolan-2-yl, 2-vinyl-1,3-dioxolan-4-yl, 3-phenyl-isoxazol-5-yl, 3-methyl-isoxazol-5-yl, 3-methoxymethyl-isoxazol-5-yl, 5-chlorothien-2-yl, 2-chlorothien-3-yl, 3,5-dichlorothien-2-yl, 2,5-dichlorothien-3-yl, 2,3-dichlorothien-4-yl, 2-chlorothien-4-yl, 2-isopropyl-1,3,4-oxadiazol-5-yl, 2-methyl-1,3,4-thiadiazol-5-yl, 5-chloro-1,2,3-thiadiazol-4-yl, thien-2-yl and thien-3-yl.

3. A cyclohexenone derivative of the formula I as set forth in claim 1, where $R^4$ is substituent selected from the group consisting of tetrahydropyran-3-yl, tetrahydropyran-4-yl, tetrahydrothiopyran-3-yl, tetrahydrothiopyran-4-yl, tetrahydrofuran-3-yl, tetrahydrothien-3-yl, pyrid-3-yl, 1,3-dioxepan-5-yl, tetrahydro-pyrano-pyranyl according to formula IIa, tetrahydrothiino-thiinyl according to formula IIa, hexahydropyranopyranyl according to formula II and hexahydrothiinothiinyl according to formula II.

4. A cyclohexenone derivative of the formula I as set forth in claim 1, where $R^3$ is thien-2-yl or thien-3-yl which is unsubstituted or substituted by one or two chlorine atoms.

5. A cyclohexenone derivative of the formula I as set forth in claim 1, where $R^1$ is hydrogen, $R^2$ is propyl, $R^3$ is 5-chlorothien-2-yl and $R^4$ is tetrahydrothiopyran-3-yl.

6. A herbicidal composition containing inert additives and an effective amount of a cyclohexenone derivative of the formula I as set forth in claim 1.

7. A herbicidal composition as set forth in claim 6, containing from 0.1 to 95 wt% of the cyclohexenone derivative.

8. A herbicidal composition as set forth in claim 6, containing a cyclohexenone derivative of the formula I, where $R^2$ is a substituent selected from the group consisting of furan-2-yl, tetrahydro-furan-2-yl, 1,3-dioxolan-2-yl, 2-phenyl-1,3-dioxolan-2-yl, 2,2-dimethyl-1,3-dioxolan-4-yl, 4,5-dimethyl-1,3-dioxolan-2-yl, 2-vinyl-1,3-dioxolan-4-yl, 3-phenyl-isoxazol-5-yl, 3-methyl-isoxazol-5-yl, 3-methoxymethyl-isoxazol-5-yl, 5-chlorothien-2-yl, 2-chlorothien-3-yl, 3,5-dichlorothien-2-yl, 2,5-dichlorothien-3-yl, 2,3-dichlorothien-4-yl, 2-chlorothien-4-yl, 2-isopropyl-1,3,4-oxadiazol-5-yl, 2-methyl-1,3,4-thiadiazol-5-yl, 5-chloro-1,2,3-thiadiazol-4-yl, thien-2-yl and thien-3-yl.

9. A herbicidal composition as set forth in claim 6, containing a cyclohexenone derivative of the formula I, where $R^4$ is substituent selected from the group consisting of tetrahydropyran-3-yl, tetrahydropyran-4-yl, tetrahydrothiopyran-3-yl, tetrahydrothiopyran-4-yl, tetrahydrofuran-3-yl, tetrahydrothien-3-yl, pyrid-3-yl, 1,3-dioxepan-5-yl, tetrahydro-pyrano-pyranyl according to formula IIa, tetrahydrothiino-thiinyl according to formula IIa, hexahydropyranopyranyl according to formula II and hexahydrothiinothiinyl according to formula II.

10. A process for combatting unwanted plant growth, wherein the unwanted plants and/or the area to be kept free from unwanted plant growth are treated with a herbicidally effective amount of a cyclohexenone derivative of the formula I as set forth in claim 1, or a salt thereof.

* * * * *